United States Patent [19]
Tau

[11] Patent Number: 4,605,781
[45] Date of Patent: Aug. 12, 1986

[54] PRODUCTION OF 2-METHYLBUTANAL
[75] Inventor: Kwoliang D. Tau, Corpus Christi, Tex.
[73] Assignee: Celanese Corporation, New York, N.Y.
[21] Appl. No.: 772,219
[22] Filed: Sep. 3, 1985
[51] Int. Cl.[4] ............................................. C07C 45/50
[52] U.S. Cl. ..................................... 568/454; 502/155
[58] Field of Search ......................... 568/454; 502/155
[56] References Cited

U.S. PATENT DOCUMENTS

| | | | |
|---|---|---|---|
| 3,239,566 | 3/1966 | Slaugh et al. | 568/454 |
| 3,965,192 | 6/1976 | Booth | 568/454 |
| 4,258,214 | 3/1981 | Barhmann et al. | 568/454 |
| 4,260,828 | 4/1981 | Morrell et al. | 568/454 |
| 4,287,370 | 9/1981 | Harris et al. | 568/454 |
| 4,482,749 | 11/1984 | Dennis et al. | 568/454 |
| 4,484,006 | 11/1984 | Menapace | 568/454 |

FOREIGN PATENT DOCUMENTS

| | | | |
|---|---|---|---|
| 762469 | 9/1971 | Belgium | 568/454 |
| 1812504 | 7/1969 | Fed. Rep. of Germany | 568/454 |
| 2037783 | 2/1972 | Fed. Rep. of Germany | 568/454 |
| 7008999 | 12/1970 | Netherlands | 568/454 |
| 1243189 | 11/1968 | United Kingdom | 568/454 |
| 1243190 | 11/1968 | United Kingdom | 568/454 |
| 1284615 | 12/1970 | United Kingdom | 568/454 |

OTHER PUBLICATIONS

Tolman, "Chemical Review", vol. 77, Feb.-Dec. 1977, pp. 313-347.
Fell et al., "Tetrahedron Letters", No. 29, pp. 3261-3266, 1968, Pergamon Press, Great Britain.

Primary Examiner—Werren B. Lone
Attorney, Agent, or Firm—S. N. Rice

[57] ABSTRACT

A continuous process for hydroformylating butene-2 so as to produce 2-methylbutanal in the presence of an halogen-free rhodium complex catalyst of the formula $RhH_m(CO)_nL_p$, wherein "L" is a trialkyl (including cycloalkyl) phosphine ligand having a cone angle within the range of 159 to 171 degrees and wherein the frequency of the $A_1$ carbonyl mode of the $Ni(CO)_3L$ in dichloromethane is within the range of 2056.1 to 2061.1 $cm^{-1}$, there being no substantial excess of free phosphorous ligand.

14 Claims, No Drawings

PRODUCTION OF 2-METHYLBUTANAL

BACKGROUND OF THE INVENTION

It is known in the prior art to hydroformylate olefins to produce aldehyde products in the presence of rhodium complex catalysts. The greatest body of the prior art deals with the hydroformylation of alpha olefins and internal olefins so as to produce a straight chain, terminally substituted aldehyde product instead of the iso- or branched chain aldehyde. Various prior art references do disclose the hydroformylation of internal olefins to produce branched chain aldehydes; however these prior art processes are not generally economically feasible because of extreme conditions of heat and pressure required, or because of low conversions or selectivities. Also, many prior art processes utilize catalysts which, while they initially produce good results, slowly degrade and become unstable in a continuous process as is normally used in commercial production. Thus "batch runs" do not always provide a proper catalyst evaluation since catalyst stability cannot be properly evaluated except in a continuous process. Further, the prior art references do not disclose a manner by which one can predict whether a particular catalyst will give good results in the production of a branched chain aldehyde.

Even though most of prior art deals with the production of a straight chain, terminally substituted aldehyde product, in many instances the branched chain aldehyde is desired. For example, branched chain aldehydes, as opposed to the straight chain isomers, are desirable as starting materials for the production of many polymer products. Thus, 2-methylbutanal, which may be produced from butene-2, is useful as the starting material for the production of isoprene.

It is thus an object of the present invention to provide a process for the hydroformylation of butene-2 to produce 2-methylbutanal with high selectivity. It is also an object of the present invention to provide a process for the hydroformylation of butene-2 to produce 2-methylbutanal under economically feasible process conditions and at high reaction rates and selectivities, and which utilizes a catalyst with good stability under continuous operating conditions. It is also an object of the present invention to provide a method by which one may predict whether or not a particular catalyst will be effective for hydroformylation of butene-2 to 2-methylbutanal, and the parameters for such a catalyst. These and other objects of the present invention will become apparent from the following description of the present invention.

SUMMARY

The foregoing and additional objects are accomplished by the present invention which in one of its aspects is a continuous process for selectively producing 2-methylbutanal by selectively hydroformylating a butene-2, which process comprises contacting, on a continuous process basis, in a hydroformylation zone:
(a) said butene-2;
(b) with carbon monoxide and hydrogen in the mole ratio of hydrogen to carbon monoxide within the range of 1/5 to 10/1;
(c) in the presence of an halogen-free rhodium complex catalyst of the empirical formula:

$$RhH_m(CO)_nL_p \quad \text{I}$$

wherein "Rh" is rhodium, "H" is hydrogen, "CO" carbon monoxide and "L" is a triorganophosphine ligand, and wherein m is 1 or 3, n is from 1 to 3, and p is 1 or 2, the sum of m, n and p being from 4 to 6, said triorganophosphine ligand being selected from the group consisting of trialkylphosphines, including tricycloalkylphosphines, wherein each of the three alkyl, including cycloalkyl groups are alike or different, and each contains from 3 to 10 carbon atoms, and wherein said triorganophosphine ligand has a cone angle within the range of 159 to 171 degrees, and, wherein the frequency of the $A_1$ carbonyl mode of the nickel tricarbonyl complex of the ligand, $Ni(CO)_3L$, in dichloromethane is within the range of 2056.1 to 2061.1 $cm^{-1}$;
(d) wherein the triorganophosphorus ligand is not in substantial excess such that there is not any substantial amount of free triorganophosphorus ligand;
(e) at a pressure within the range of about 6 to 30 atmospheres absolute;
(f) at a temperature within the range of about 80° C. to 150° C.;
(g) so as to produce hydroformylation products of said butene-2 wherein the mole ratio of 2-methylbutanal to other oxygenated products is at least 4/1; and continuously recovering from said hydroformylation zone said hydroformylation products having a said mole ratio of 2-methylbutanal to other oxygenated products of at least 4/1.

DETAILED DESCRIPTION OF THE INVENTION

As may be seen from the above summary, the present invention is a hydroformylation accomplished under specific conditions of pressure and temperature, and in the presence of a specified type of complex catalyst. All of the conditions and limitations recited are critical to the invention, and any substantial deviation from the conditions and limits specified will cause adverse results. The hydroformylation of an olefin in the presence of a rhodium complex catalyst to produce an aldehyde product is well known, and most of the details as to such will not be discussed herein because of the large body of prior art pertaining thereto. The description herein will be limited mainly to the process limitations and catalyst limitations that must be observed in order to accomplish the high selectivity and high conversion desired. In other words, unless otherwise specified herein, conventional hydroformylation conditions and procedures may be utilized.

The invention is useful for hydroformylation of butene-2 (both cis and trans) to produce 2-methylbutanal. As between the two isomers, it has been found that cis-2-butene reacts faster than trans-2-butene, however they result in similar aldehyde product compositions. If the feedstock available contains olefins other than a butene-2, then most of these other olefins need to be removed prior to being fed to the hydroformylation zone. Butadiene is especially harmful to the process and as much butadiene as reasonably possible should be removed. Purging may be necessary to prevent buildup of butadiene and other unwanted components. It is thus preferred that at least 95%, preferably at least 98%, of the olefin feed to the hydroformylation zone in the present invention be butene-2. Excess amounts of other olefins may adversely affect selectivities. The butene-2 may be fed to the reaction zone as either a liquid or a gas.

A commercially available butene feedstock may consist of a mixture of butene-1 and butene-2, and such a feedstock of mixed butenes may be readily isomerized to a thermodynamic mix which will contain greater than 95% of butene-2 and less than 5% of butene-1. The isomerization may be carried out in the presence of a double bond isomerization catalyst which does not cause any appreciable chain branching. Such catalysts are well known in the art and the method of accomplishing such does not constitute a part of the present invention. Isobutylene may also be present in a commercially available feedstock, and its presence will not interfere with the invention. If not removed, the isobutylene will be converted to 3-methylbutanal. For economic reasons, however, it will generally be preferable to remove the isobutylene from the feedstock prior to the hydroformylation.

The hydroformylation process of the invention should be conducted at pressures within the range of about 6 to 30 atmospheres absolute, although the preferred range is from about 15 to 25 atmospheres absolute. The relatively low pressures required in the present invention make the process more feasible from an economic standpoint than some prior art processes which operate at pressures of about 50 atmospheres. Although such has not been definitely established, it is believed that if pressures are too great then the rhodium complex catalyst may be adversely affected under the conditions at which the present invention is conducted.

The total pressure in the hydroformylation zone will be equal to the sum of the partial pressures of the reactants and of the products, and of any inert gases that may be present. Two of the gases which will be present and contribute to the total pressure are the reactants carbon monoxide and hydrogen, the combination of carbon monoxide and hydrogen generally being referred to in the art as "synthesis gas". Although the ratio of these two reactants may vary, the mole ratio of hydrogen to carbon monoxide should not be less than 1/1; that is the partial pressure of the carbon monoxide should not exceed the partial pressure of the hydrogen. Generally, the mole ratio of hydrogen to carbon monoxide should be within the range of about 1/1 to 10/1, preferably within the range of about 1.5/1 to 3/1. Generally, lower ratios of hydrogen to carbon monoxide will give better selectivity to 2-methylbutanal. Of the total pressure present in the hydroformylation zone, from about 40% to 95% should result from the combined partial pressures of the carbon monoxide and hydrogen.

The butene-2 will also contribute to the total pressure in the hydroformylation zone, and the partial pressure of the butene-2 may be greater or lesser than the pressure of the synthesis gas. Thus the amount of synthesis gas may be greater or lesser than the amount of butene-2 present in the reaction zone, and the mole ratio of butene-2 to synthesis gas is not particularly critical. In the event any inert gases, such as nitrogen, are present in the hydroformylation zone, such should not exert a partial pressure in excess of 60% of the total pressure.

The temperature under which the hydroformylation is conducted should be within the range of about 80° C. to 150° C., although the temperature range is preferably from about 105° C. to 130° C. Below about 80° C., the reaction rate is generally too slow to be of commercial interest, and above about 150° C. selectivity to the desired branched aldehyde is low. Also at temperatures above about 150° C., substantial catalyst deactivation occurs.

The catalyst utilized in the present invention is a rhodium complex catalyst of the empirical formula:

$$RhH_m(CO)_nL_p \qquad 1$$

wherein "Rh" is rhodium, "H" is hydrogen, "CO" carbon monoxide and "L" is a triorganophosphine ligand, and wherein m is 1 or 3, n is from 1 to 3, and p is 1 or 2, the sum of m, n and p being from 4 to 6. The triorganophosphine ligand must be one selected from the group consisting of trialkylphosphines, including tricycloalkylphosphines, wherein each of the three alkyl (including cycloalkyl) groups are alike or different (but preferably alike) and each contains from 1 to 8 carbon atoms. The triorganophosphine ligand must be one wherein the cone angle is within the range of 159 to 171 degrees, and which has a frequency of the $A_1$ carbonyl mode of $Ni(CO)_3L$ in dichloromethane within the range of 2056.1 to 2061.1 cm$^{-1}$. Rhodium complex catalysts of this general class are well known in the literature for hydroformylation of olefins, and any of the conventional techniques may be utilized for the preparation of such. As in the prior art, the complex catalyst may be formed prior to the hydroformylation or may be formed in-situ in the hydroformylation zone.

While the prior art literature does disclose the general class of rhodium complex catalysts listed above, the prior art was generally concerned with preparation of normal aldehydes from alpha or internal olefins, and the prior art does not teach a method for choosing a catalyst for obtaining branched-chain aldehydes which will give a combination of high conversion rate, high selectivity to a branched-chain aldehyde and good catalyst stability. Those in the art will recognize that high selectivity and high conversion may be all that are needed in a batch run; however good catalyst stability is also absolutely necessary in a commercial process wherein product is produced under continuous operating conditions. The inventor has unexpectedly discovered that to have the three qualities of high selectivity to a branched-chain aldehyde, high conversion rate and good stability, the trialkylphosphine must both have a cone angle within the range of 159 to 171, and a frequency of the $A_1$ carbonyl mode of the nickel tricarbonyl phosphine complex in dichloromethane within the range of 2056.1 to 2061.1. Thus a phosphine having a cone angle within the range of 159 to 171, but a said frequency of the $A_1$ carbonyl mode of the nickel tricarbonyl phosphine complex outside the range of 2056.1 to 2061.1, will not be satisfactory. Further, the process must be operated within the parameters set forth herein, and in particular there must be no substantial amount of free triorganophosphorous ligand presented in the hydroformylation zone.

The cone angle is a measure of steric properties of the phosphine, while the frequency is a measure of electronic properties or basicity of the phosphine. A very through discussion of cone angle and frequency measurements of said $A_1$ carbonyl mode of the nickel tribarbonyl phosphine complex can be found in the following publication: Chadwick A. Tolman, "Steric Effects of Phosphorus Ligands in Organometallic Chemistry and Homogeneous Catalysis," *Chemical Reviews*, 1977, Vol. 77, No. 3; pp. 313-348. All references in the Specification and the Claims to "cone angle" and "frequency"

are as utilized in the Tolman article, and as such are measured in the Tolman article. As stated in the Tolman article the cone angle, in general terms, is the smallest angle of a cone (with its apex at a specified point in the phosphine ligand) which would contain all of the alkyl or cycloalkyl groups attached to the phosphorus atom. Tolman also points out that the frequency of the $A_1$ carbonyl mode of $Ni(CO)_3L$ in dichloromethane was chosen because the $Ni(CO)_3L$ forms rapidly upon mixing $Ni(CO)_4$ and L (the ligand).

Suitable trialkylphosphines and tricycloalkyl phosphines which have the proper cone angle and have the proper basicity are set forth in Table I.

TABLE I

| Phosphine | Cone Angle (Degrees) | Frequency $(cm^{-1})$ |
|---|---|---|
| Tricyclohexylphosphine | 170 | 2056.4 |
| Tri-sec-butylphosphine | 160 | 2058–2060* |
| Tri-isopropylphosphine | 160 | 2059.2 |

*estimated

The especially preferred phosphine for use in the present invention is tricyclohexylphosphine.

The following Table II lists various triorganophosphines, and their respective cone angles and frequencies, which are not suitable for the present invention because either their cone angle or their frequency, or both, are not within the proper range. Also, one of the phosphine, di-tert-butylphenylphosphine, is not within the scope of the invention and not satisfactory for a catalyst because it includes an aryl group, even though its cone angle and frequency are within the desired ranges.

TABLE II

| Phosphines | Cone Angle (Degrees) | Frequency $(cm^{-1})$ |
|---|---|---|
| Di-tert-butylphenylphosphine | 170 | 2060.4 |
| Tribenzylphosphine | 165 | 2066.4 |
| Tri-tert-butylphosphine | 182 | 2056.1 |
| Trimethylphosphine | 118 | 2064.1 |
| Tri-n-butylphosphine | 132 | 2060.3 |
| Triisobutylphosphine | 143 | 2059.7* |
| Triphenylphosphine | 145 | 2068.9 |
| Triphenylphosphite | 128 | 2085.3 |

*estimated

As used herein the term "conversion" means mole percent conversion, and is calculated by multiplying the moles of butene-2 converted to another product times 100 and dividing such by the moles of butene-2 fed. As used herein the term "efficiency" of a particular product means mole percent efficiency, and is calculated by dividing the number of moles of a particular product obtained by the number of moles of butene-2 consumed in the reaction.

In conducting the process, the catalyst will usually be present in solution, since the hydroformylation is generally conducted as a liquid phase homogenous reaction. The solvent utilized may comprise any of the various inert solvents commonly utilized, such as toluene. Other commonly used inert solvents are high boiling liquid condensation products rich in hydroxylic compounds, polymeric aldehyde condensation products, polyalphaolefins, and the like.

The rhodium may be introduced into the reaction zone in any convenient manner. For example the rhodium salt of an organic acid may be combined with the ligands in the liquid phase and then subjected in the reaction zone to the synthesis gas. Alternatively, the catalyst can be prepared from a carbon monoxide complex of rhodium, such as hexarhodium hexadecacarbonyl, by heating such with the ligands. Also, and the method of choice, is to introduce into the reaction zone as a catalyst precursor, a rhodium complex such as the rhodium dicarbonyl complex formed with acetylacetonate ligand, and then introducing separately to the reaction zone the triorganophosphine ligand. The general method of forming similar catalysts is disclosed and discussed in various literature such as U.S. Pat. No. 4,484,006 issued Nov. 20, 1984 to Henry R. Menapace; U.S. Pat. No. 4,287,370 issued Sept. 1, 1981 to Norman Harris, et al; and in British Patent Specification 1,243,189 of Malcolm John Lawrenson, et al, published Aug. 18, 1971. Other references to similar catalysts are in the article by B. Fell, et al, Tetrahedron Letters, 1968, pages 3261-3266; U.S. Pat. No. 4,260,828 issued Apr. 7, 1981 to Morrell, et al; U.S. Pat. No. 4,268,688 issued May 19, 1981 to Tinker, et al; U.S. Pat. No. 4,258,214 issued Mar. 24, 1981 to Bahrmann, et al; U.S. Pat. No. 3,965,192 issued June 22, 1976 to Frank B. Booth; European Patent Application Publication 0-080-449-A1 published June 1, 1983 to Monsanto Chemical Company; U.S. Pat. No. 3,239,566 issued Mar. 8, 1966 to Slaugh et al; and U.S. Pat. No. 4,482,749 issued Nov. 13, 1984 to Dennis et al.

Even though a wide variety of precursors may be used to form the catalyst, a halogen-containing precursor must not be used because such will result in at least residual amounts of halogen in the catalyst and/or reaction system. Halogens, even in small amounts, will prove deleterious to the reaction. Also, if a rhodium-containing precursor wherein the rhodium is present as rhodium III (that is in the +3 oxidation state), then the catalyst should be subjected to reducing conditions so as to reduce the rhodium III to rhodium I. Thus, for example, where $Rh_2O_3$ is utilized as a precursor, the catalyst should be pretreated at high pressures to reduce the oxidation state of the rhodium, and then the reaction can be run at the desired relatively low pressures disclosed herein. Conversely, if the rhodium is not reduced from rhodium III to rhodium I, then the hydroformylation would have to be conducted at undesirably high pressures outside the scope of the present invention.

The preferred catalyst for use in the invention is one of Formula I above which has been prepared utilizing a precursor consisting of a rhodium complex with a beta-diketone, such as the rhodium dicarbonyl complex formed with acetylacetonate ligand. The beta-diketone utilized for forming the complex may be any of those generally available. Suitable beta-diketones include acetylacetone, dibenzoylmethane, benzoylacetone, dipivaloylmethane, 3-alkyl-2,4-pentanedione, and 2-acetylcylohexanone. Preferably the beta-diketone will be composed only of carbon, hydrogen and oxygen and will be free of ethylenic and acetylenic unsaturation. The especially preferred beta-diketone is acetylacetone.

Even though the process of the present invention is similar to many of the prior art processes, its differences from the prior art are critical and account for the high selectivity, high conversion and good catalyst stability which provide relatively economical conditions of operation. The most important differences between the invention and the prior art are the triorganophosphine limitations, lower pressures involved, and the absence of any material amounts of free phosphine ligand. Unlike prior art processes which require large excess of the phosphine, the present invention will under the specified process, provide satisfactory results only in the absence of any substantial amounts of free phosphine ligand. At the low pressures and other process conditions specified herein, excess phosphine causes substantial decreases in reaction rate.

EXAMPLES I-VI

Examples I-VI below show the results of several batch runs which were made to evaluate different rhodium phosphine complex catalysts. All catalysts were formed using a rhodium dicarbonyl complex formed with acetylacetonate ligand, except as indicated, with the particular phosphine ligand used being indicated in each example. Each of the runs was conducted in a batch autoclave of 300 ml. capacity fitted with a stirrer and a cooling coil. The rhodium catalyst, reaction solvent and phosphine were charged to the autoclave and the autoclave then sealed and purged with nitrogen. The total volume charged in each batch run was 80 ml, excluding butene-2. If the phosphine was air sensitive, it was added only after the autoclave had been purged with nitrogen. The autoclave was then brought to reaction temperature and the butene-2 and synthesis gas introduced. The amount of butene-2 added in each batch run was 16.6 grams. During the reaction additional synthesis gas was introduced to maintain a constant pressure. The amount of synthesis gas used was determined by monitoring the pressure drop in the synthesis gas reservoir. After a predetermined time the reaction was terminated. Product samples were removed following the termination of the reaction and analyzed by gas chromatography. The results of the various batch runs, and reaction parameters for such, are set forth in the following Examples I to VI. In each of the Examples, the conversion ("Conv.") is of butene-2, the efficiency ("Eff.") is of butene-2 to C5 aldehydes, the B/L is the mole ratio of 2-methylbutanal to n-pentenal in the product, and all times are in minutes. The half-life, in minutes, shown in the Examples is the time necessary for half of the butene-2 to be converted, and is a measure of the reaction rate, with a longer half-life indicating a slower reaction rate.

EXAMPLE I

A series of runs were conducted to show the effect of phosphine concentration on hydroformylation of butene-2 using a rhodium complex catalyst formed from a tricyclohexylphosphine ligand. All of the runs were conducted in a toluene solvent at a temperature of 110° C., a pressure of 317 psig, and utilizing a synthesis gas having a hydrogen to carbon monoxide mole ratio of 1/1. The catalyst complex was present in sufficient amount to supply 1 millimole of rhodium. In Run No. 1, no phosphine was present, with the phosphorus to rhodium (P/Rh) mole ratio being indicated in the other runs. Results are set forth in the following Table I.

TABLE I

| Run No. | P/Rh | React Time | Conv. % | Eff. % | B/L | Half-Life |
|---|---|---|---|---|---|---|
| 1 | 0 | 84 | 56.2 | 95.2 | 1.3 | 74.0 |
| 2 (a) | 1 | 30 | 89.6 | 98.4 | 9.3 | 6.5 |
| 3 | 2 | 60 | 88.0 | 98.3 | 36.5 | 17.0 |
| 4 (a) | 2 | 60 | 90.7 | 98.0 | 37.5 | 8.0 |

(a) The catalyst was pretreated with 317 psig syn gas (H2/CO = 1) at 110° C. for one hour.

Results from the above runs in Table I show the effect of phosphine concentration, and that a 1/1 P/Rh mole ratio is sufficient to give a highly active and selective catalyst. Run Nos. 2 and 4 also indicate pretreatment with synthesis gas produced a more active catalyst. When the P/Rh mole ratio was increased to 2/1, the B/L ratio did increase at the expense of a slight decrease in catalyst activity.

EXAMPLE II

Another series of runs were made to show the effect of phosphine concentration on hydroformylation of butene-2 using a rhodium complex catalyst formed from a tricyclohexylphosphine ligand. The catalyst was pretreated at 120° C. for one hour with 317 psig synthesis gas having a hydrogen to carbon monoxide mole ratio of 1/1. All of the runs in this Example II were conducted in a toluene solvent at a temperature of 120° C., a pressure of 200 psig, and utilizing a synthesis gas with a hydrogen to carbon monoxide mole ratio of 3/1. In each of the runs the amount of rhodium charged was held constant at 1 millimole. The results in the following Table II show that the higher the P/Rh mole ratio, the lower the reaction rate (as indicated by the half-life). Addition of excess phosphine did not proportionally increase the B/L ratio of 2-methylbutanal to n-pentanal, and indicates that excess phosphine is not needed.

TABLE II

| Run No. | P/Rh | React Time | Conv. % | Eff. % | B/L | Half-Life |
|---|---|---|---|---|---|---|
| 1 | 1 | 30 | 99.0 | 96.1 | 6.3 | 2.0 |
| 2 | 2 | 30 | 94.7 | 98.3 | 7.1 | 3.5 |
| 3 | 4 | 30 | 93.7 | 98.3 | 6.7 | 5.0 |
| 4 | 10 | 30 | 89.4 | 98.5 | 5.9 | 9.0 |
| 5 | 15 | 30 | 84.3 | 98.2 | 5.9 | 13.0 |
| 6 | 30 | 40 | 72.3 | 98.2 | 5.1 | 30.0 |

EXAMPLE III

Several runs were conducted using a rhodium complex catalyst formed from a triphenylphosphine, which is not one of the organophosphine ligands covered by the present invention because its cone angle is outside the desired range as is the frequency of the $A_1$ carbonyl mode of its nickel tricarbonyl complex described above. The runs were made to illustrate that the triphenylphosphine does not form a suitable commercially feasible catalyst for butene-2 hydroformylation to 2-methylbutanal in accordance with the present invention. In this Example, several runs were made in a toluene solvent, at a temperature of 110° C., a pressure of 317 psig, and utilizing a synthesis gas with a 1/1 mole ratio of hydrogen to carbon monoxide. In this Example no acetylacetonate was utilized in forming the complex catalyst, and the catalyst was of the formula H(CO)RhL$_3$-L wherein "L" is triphenylphosphine. The concentration of the H(CO)RhL$_3$ catalyst precursor was varied as was the additional triphenylphosphine (indicated in the following Table III as "Free PPh3"). The results in the following Table III show that the catalyst has low activity, especially after synthesis gas treatment.

TABLE III

| Run No. | H(CO)RhL3 Complex mmole | Free PPh3 mmole | React Time | Conv. % | Eff. % | B/L | Half-life |
|---|---|---|---|---|---|---|---|
| 1 | 2.50 | 17.50 | 44 | 61.9 | 98.8 | 12.9 | 27 |
| 2 | 2.50 | 42.50 | 44 | 53.9 | 98.0 | 8.4 | 41 |
| 3 | 2.50 | 67.50 | 54 | 51.9 | 98.6 | 6.2 | 53 |
| 4 | 1.00 | 7.00 | 66 | 65.7 | 98.9 | 15.7 | 43 |

TABLE III-continued

| Run No. | H(CO)RhL₃ Complex mmole | Free PPh3 mmole | React Time | Conv. % | Eff. % | B/L | Half-life |
|---|---|---|---|---|---|---|---|
| 5 | 1.00 | 17.00 | 68 | 55.5 | 99.4 | 14.8 | 52 |
| 6 | 1.00 | 27.00 | 89 | 62.6 | 98.3 | 14.4 | 74 |
| 7 | 1.00 | 87.00 | 149 | 54.6 | 99.4 | 4.9 | 127 |
| 8 | 0.05 | — | 50 | 69.0 | 99.2 | 3.6 | 43 |
| 9 | 0.05 | 0.35 | 50 | 54.7 | 98.4 | 8.3 | 72+ |
| 10 | 0.05 | 0.85 | 50 | 32.8 | 97.5 | 9.6 | 126+ |
| 11 | 0.05 | 1.35 | 50 | 30.2 | 97.2 | 10.4 | 139+ |
| 12 | 0.05 | 2.85 | 50 | 27.5 | 97.0 | 13.1 | 154+ |
| 13 | 0.05 | 5.85 | 50 | 20.2 | 96.1 | 14.6 | 204+ |
| Catalyst Activities before and after Syn Gas Treatment | | | | | | | |
| 14 | 2.50 | 17.50 | 44 | 61.9 | 98.8 | 12.9 | 27 |
| 15 | 2.50 (a) | 17.50 | 49 | 27.4 | 98.4 | 10.5 | 117+ |
| 16 | 1.00 | 87.00 | 149 | 54.6 | 99.4 | 4.9 | 127 |
| 17 | 1.00 (b) | 87.00 | 161 | 53.2 | 98.6 | 4.6 | 358+ |
| 18 | 0.05 | 4.35 | 227 | 54.1 | 99.6 | 17.7 | 205 |
| 19 | 0.05 (b) | 4.35 | 180 | 17.7 | 98.6 | 21.6 | 695+ |

(a) The catalyst had been pretreated with 317 psig syn gas (H2/CO = 1) at 110° C. for 4 hours.
(b) The catalyst had been pretreated with 317 psig syn gas (H2/CO = 1) at 110° C. for 8 hours.

EXAMPLE IV

Several runs were made to show the effects of a synthesis gas pretreatment, pressure, temperature, synthesis gas composition and rhodium concentration on the performance of a catalyst formed from a tricyclohexylphosphine ligand. The phosphorus to rhodium mole ratio of the catalyst was 2/1, and the catalyst was utilized in such amounts to provide one millimole of rhodium, except as indicated. The catalyst was in some cases pretreated with synthesis gas having a hydrogen to carbon monoxide mole ratio of 1/1, as indicated. Each run was conducted for 30 minutes in a polyalphaolefin solvent at a temperature of 110° C. (except Run No. 5 at 120° C.), at a pressure of 300 psig (except Run No. 4 at 200 psig), and utilizing a synthesis gas having a hydrogen to carbon monoxide mole ratio of 2/1 (except Run No. 6 at 1/1).

TABLE IV

| Run No. | Rh mmole | Conv. % | Eff. % | B/L | Half-life |
|---|---|---|---|---|---|
| 1 | 1.0 | 90.9 | 98.4 | 25.3 | 8.0 |
| 2 | 1.0(a) | 94.4 | 98.0 | 26.4 | 4.5 |
| 3 | 1.0(d) | 94.8 | 98.2 | 21.2 | 4.5 |
| 4 | 1.0(b) | 95.0 | 98.3 | 13.5 | 5.0 |
| 5 | 1.0(c) | 98.2 | 96.5 | 13.5 | 2.5 |
| 6 | 1.0(a)(e) | 79.2 | 98.3 | 32.4 | 7.5 |
| 7 | 0.5(a) | 84.8 | 98.7 | 23.5 | 9.5 |

(a) The catalyst was pretreated with 300 psig syn gas (H₂/CO = 1) at 110° C. for 1 hour.
(b) The catalyst was pretreated with 200 psig syn gas (H₂/CO = 1) at 110° C. for 1 hour. Run No. 4 was conducted at a pressure of 200 psig.
(c) The catalyst was pretreated with 300 psig syn gas (H₂/CO = 1) at 120° C. for 1 hour. Run No. 5 was conducted at a temperature of 120° C.
(d) The catalyst was pretreated with 300 psig syn gas (H₂/CO = 1) at 110° C. for 16 hours.
(e) H₂/CO = 1

EXAMPLE V

Several runs were made to show the performance of a catalyst formed from a tri-isopropylphosphine ligand under different reaction conditions. The phosphorus to rhodium mole ratio of the catalyst was 2/1, and the catalyst was utilized in such amounts to provide one millimole of rhodium, except as indicated. The catalyst was in some cases pretreated with synthesis gas having a hydrogen to carbon monoxide mole ratio of 1/1, as indicated. Each run was conducted for 30 minutes in a polyalphaolefin solvent at a temperature of 110° C. (except Run No. 5 at 120° C.), at a pressure of 300 psig (except Run No. 4 at 200 psig), and utilizing a synthesis gas having a hydrogen to carbon monoxide mole ratio of 2/1 (except Run No. 6 at 1/1).

TABLE V

| Run No. | Rh mmole | Conv. % | Eff. % | B/L | Half-life |
|---|---|---|---|---|---|
| 1 | 1.00 | 97.8 | 98.2 | 17.7 | 3.5 |
| 2 | 1.00 (a) | 98.0 | 98.0 | 18.4 | 2.5 |
| 3 | 1.00 (d) | 97.7 | 97.8 | 17.3 | 2.5 |
| 4 | 1.00 (b) | 98.1 | 98.0 | 8.8 | 3.0 |
| 5 | 1.00 (c) | 98.3 | 96.3 | 8.1 | 1.5 |
| 6 | 1.00 (a) (e) | 83.3 | 98.1 | 22.8 | 4.5 |
| 7 | 0.50 (a) | 94.3 | 98.4 | 18.2 | 4.0 |

(a) The catalyst was pretreated with 300 psig syn gas (H2/CO = 1) at 110° C. for 1 hour.
(b) The catalyst was pretreated with 200 psig syn gas (H2/CO = 1) at 110° C. for 1 hour. Run No. 4 was conducted at a pressure of 200 psig.
(c) The catalyst was pretreated with 300 psig syn gas (H2/CO = 1) at 120° C. for 1 hour. Run No. 5 was conducted at a temperature of 120° C.
(d) The catalyst was pretreated with 300 psig syn gas (H2/CO = 1) at 110° C. for 17 hours.
(e) H2/CO = 1

EXAMPLE VI

Several runs were made to evaluate various phosphine ligands, some of which were within the scope of the invention and some outside the scope of the invention. All of the complex catalysts utilized were formed so as to provide a phosphorus to rhodium mole ratio of 2/1. Each run was conducted in a toluene solvent at a temperature of 110° C., a pressure of 317 psig and utilizing a synthesis gas having a hydrogen to carbon monoxide mole ratio of 1/1. For each catalyst evaluated, one run was conducted wherein the catalyst had not been pretreated with the synthesis gas, and a second run was conducted wherein the catalyst had been pretreated with the synthesis gas at about 110° C. and 317 psig (H₂/CO=1) for a period of about 16 to 17.5 hrs. The catalyst was used in such an amount as to provide one millimole of rhodium, except Run Nos. 7 and 8 wherein triphenylphosphine was evaluated which utilized a 0.5 millimole concentration of rhodium.

TABLE VI

| Run No. | Pretreat hours | React Time | Conv. % | Eff. % | B/L | Half-life |
|---|---|---|---|---|---|---|
| tricyclohexylphosphine | | | | | | |
| 1 | 0 | 60 | 88 | 98 | 37 | 17.0 |
| 2 | 17.5 | 30 | 83 | 99 | 40 | 8.5 |
| tri-isopropylphosphine | | | | | | |
| 3 | 0 | 30 | 86 | 99 | 34 | 8.0 |
| 4 | 17 | 30 | 86 | 99 | 30 | 6.0 |
| tri-sec-butylphosphine | | | | | | |
| 5 | 0 | 30 | 88 | 98 | 32 | 7.0 |
| 6 | 17 | 30 | 86 | 98 | 33 | 6.5 |
| triphenylphosphine | | | | | | |
| 7 | 0 | 26 | 64 | 99 | 8 | 11.0 |
| 8 | 16 | 59 | 4 | 89 | 99+ | 1445+ |
| di-tert-butylphenylphosphine | | | | | | |
| 9 | 0 | 30 | 88 | 99 | 11 | 4.5 |
| 10 | 17 | 30 | 88 | 99 | 12 | 6.5 |
| tri-n-butylphosphine | | | | | | |
| 11 | 0 | 22 | 65 | 98 | 55 | 18.0 |
| 12 | 16 | 59 | 83 | 98 | 54 | 21.0 |
| tri-tert-butylphosphine | | | | | | |
| 13 | 0 | 24 | 90 | 98 | 8 | 3.5 |
| 14 | 16 | 30 | 89 | 98 | 9 | 5.0 |
| triisobutylphosphine | | | | | | |
| 15 | 0 | 17 | 72 | 99 | 26 | 10.0 |
| 16 | 17 | 34 | 67 | 98 | 23 | 28.0 |

TABLE VI-continued

| Run No. | Pre-treat hours | React Time | Conv. % | Eff. % | B/L | Half-life |
|---|---|---|---|---|---|---|
| | | trimethylphosphine | | | | |
| 17 | 0 | 30 | 13 | 93 | 63 | 176+ |
| 18 | 17 | 30 | 13 | 92 | 58 | 199+ |
| | | tribenzylphosphine | | | | |
| 19 | 0 | 30 | 89 | 86 | 4 | 6.5 |
| 20 | 17 | 30 | 77 | 99 | 7 | 13.0 |
| | | triphenylphosphite | | | | |
| 21 | 0 | 20 | 89 | 99 | 3 | 2.0 |
| 22 | 16 | 50 | Inactive Catalyst; No Aldehyde Produced | | | |

The results from Table VI show the superior catalytic performances of catalysts formed from organophosphine ligands within the scope of the invention, that is tricyclohexyphosphine, tri-isopropylphosphine, and tri-sec-butylphosphine. The other phosphine ligands evaluated in Table VI were outside the scope of the invention and did not perform satisfactorily from a commercial standpoint in terms of selectivity, conversion and catalyst stability. The di-tert-butylphenylphosphine, while having a cone angle and frequency within the desired range, is outside the scope of the invention since it is not trialkyl but instead contains an aryl group which is undesirable. The results of Table VI indicate more active catalysts are produced with catalysts formed from tricyclohexylphosphine, triisopropylphosphine, and tri-sec-butylphosphine after the contact with synthesis gas.

EXAMPLES VII–X

Several runs were made to evaluate different catalysts under continuous operating conditions. In each run, hydrogen, carbon monoxide, nitrogen and a vaporized butene-2 feed were mixed and then continuously charged to the reactor. The butene-2 was passed through a guard bed prior to being charged to the reactor in order to remove chlorides, acetylene and other impurities. The mixture of carbon monoxide, hydrogen and nitrogen was passed through a guard bed to remove oxygen prior to being mixed with the butene-2. The reactor was an upright, jacketed cylindrical tube constructed of Type 316 stainless steel with no internal parts, having a total volume of about 3,692 ml. Prior to starting the run, the reactor was purged with nitrogen and then charged with the catalyst and solvent, and the gas feed was sparged into the catalyst solution. Temperature in the reactor was maintained by circulating heated ethylene glycol through the jacket of the reactor. Aldehyde product was taken overhead along with unreacted gas, and then passed through a condenser operated at about 20° C. such that the aldehyde product condensed and was recovered as liquid product. The gaseous overhead from the condenser was not recycled to the reactor.

An on-line continuous analyzer constantly measured compositions of feed gas and of the overhead stream removed from the reactor. Samples of liquid aldehyde product were taken periodically and analyzed by gas chromatography for aldehyde and also analyzed by atomic absorption spectroscopy for rhodium content.

In each run, after the catalyst was charged to the reactor, synthesis gas was passed (at reaction temperature and pressure) through the reactor and catalyst-solvent mixture for about four to eight hours before beginning the charging of butene-2.

In each of the following Examples VII–X, the data presented was that taken after a steady state of the system was reached, with times indicated in each Example being the time, in hours, elapsed after butene-2 first began to be charged to the reactor (time zero). Each sample taking covered a three to six hour, more or less, time period as indicated. In the following Examples and Tables, "Vol. of Soln" is the volume of Solution in the reaction, "B/L" is the mole ratio of 2-methylbutanal to n-pentanal in the product, "Ald/Rh,hr" is a measure the catalyst activity expressed in grams aldehyde produced per gram of rhodium per hour, "Rh Conc." is rhodium concentration, "SCFH" is standard cubic feet per hour as measured at 32° F. and atmospheric pressure, "BU-2" is the butene-2 feedstream, "2MBA" is 2-methylbutanal, and "n-PA" is n-pentanal. In each of the following examples the catalyst was formed using a rhodium dicarbonyl complex formed with acetylacetonate ligand, with the particular phosphine ligand used being indicated in each Example.

EXAMPLE VII

The following Table VII shows the results of a continuous run utilizing a catalyst formed using tricylcohexylphosphine, the catalyst having a phosphorus/rhodium mole ratio of 2/1. Feed gas temperature was maintained at about 260° F. From Table VII it may be seen that the catalyst gave excellent results and stability. As indicated in Table VII, after about 88 hours a feedstock change occurred. It may be seen that the higher butene-1. concentration in the new feedstock adversely affected the reaction and resulted in a lower B/L ratio.

EXAMPLE VIII

The following Table VIII shows the results of a continuous run utilizing a catalyst formed using tri-sec-butylphosphine, the catalyst having a phosphorus/rhodium mole ratio of 2/1. Feed gas temperature was maintained at about 260° F. Table VIII indicates excellent results and good catalyst stability.

EXAMPLE IX

The following Table IX shows the results of a continuous run utilizing a catalyst formed using triisopropylphosphine, the catalyst having a phosphorus/rhodium mole ratio of 2/1. The feed gas was maintained at about 261° F. Table IX indicates excellent results were obtained with good catalyst stability.

EXAMPLE X

The following Table X shows the results of a continuous run utilizing a catalyst formed using tri-n-butylphosphine, which is not one of the phosphine ligands within the scope of the invention. The catalyst had a phosphorus/rhodium mole ratio of 2/1. The feed gas was maintained at about 260° F. As indicated in Table X, neither the catalyst activity nor the B/L ratio was satisfactory when utilizing the catalyst formed using a tri-n-butylphosphine ligand.

TABLE VII

| Time hrs | Reactor Press psig | Reactor Temp °F. | Vol of Soln ml | Rh Conc g/L | Ald Rh,hr g/g/hr | B/L | Feed Rate, SCFH CO | H2 | N2 | BU-2* |
|---|---|---|---|---|---|---|---|---|---|---|
| 55–59 | 321 | 231 | 1256 | 1.97 | 316 | 19.07 | 45.23 | 90.41 | 28.17 | 24.03 |
| 59–63 | 321 | 231 | 1256 | 1.97 | 315 | 18.92 | 45.17 | 90.36 | 28.14 | 24.00 |
| 63–67 | 321 | 231 | 1256 | 1.97 | 314 | 18.81 | 45.10 | 90.25 | 28.11 | 24.00 |
| 76–80 | 319 | 231 | 1402 | 1.76 | 360 | 15.61 | 34.17 | 101.44 | 27.93 | 24.25 |
| 80–84 | 319 | 231 | 1402 | 1.76 | 360 | 15.62 | 34.16 | 101.30 | 27.98 | 24.26 |
| 84–88 | 319 | 230 | 1402 | 1.76 | 354 | 15.62 | 34.12 | 101.39 | 28.00 | 24.26 |
| Feedstock Change** | | | | | | | | | | |
| 111–117 | 326 | 231 | 1691 | 1.46 | 459 | 11.17 | 40.82 | 121.15 | 40.66 | 21.15 |
| 125–129 | 327 | 231 | 1691 | 1.46 | 477 | 11.34 | 40.87 | 121.26 | 40.82 | 21.52 |
| 149–153 | 299 | 230 | 1458 | 1.70 | 401 | 9.75 | 41.06 | 121.29 | 41.01 | 21.65 |
| 172–176 | 300 | 230 | 1336 | 1.85 | 353 | 10.55 | 53.77 | 108.19 | 40.74 | 21.61 |
| 176–180 | 300 | 230 | 1336 | 1.85 | 354 | 10.54 | 53.91 | 108.14 | 40.83 | 21.59 |
| 180–184 | 300 | 231 | 1336 | 1.85 | 353 | 10.60 | 53.94 | 108.12 | 40.80 | 21.59 |
| 202–206 | 200 | 212 | 1170 | 2.11 | 154 | 8.44 | 27.48 | 81.12 | 27.50 | 14.53 |
| 206–225 | 199 | 212 | 1170 | 2.11 | 153 | 8.37 | 27.35 | 80.88 | 27.35 | 14.55 |
| 225–232 | 198 | 212 | 1170 | 2.11 | 154 | 8.25 | 27.33 | 81.14 | 27.47 | 14.53 |

*The butene-2 feed contained about 0.5 mole % butene-1 and 31.5 mole % n-butane
**The butene-2 feed contained about 2.8 mole % butene-1 and 4.3 mole % n-butane

TABLE VIII

| Time hrs | Reactor Press psig | Reactor Temp °F. | Vol of Soln ml | Rh Conc g/L | Ald Rh,hr g/g/hr | B/L | Feed Rate, SCFH CO | H2 | N2 | BU-2* |
|---|---|---|---|---|---|---|---|---|---|---|
| 4–10 | 300 | 231 | 1100 | 2.25 | 447 | 7.07 | 54.33 | 108.17 | 44.08 | 18.51 |
| 14–18 | 300 | 231 | 1100 | 2.25 | 432 | 6.86 | 54.31 | 107.92 | 43.96 | 18.51 |
| 24–37 | 300 | 231 | 1100 | 2.25 | 422 | 6.67 | 54.34 | 108.10 | 44.05 | 18.51 |
| 40–47 | 300 | 230 | 1100 | 2.25 | 402 | 6.56 | 54.44 | 108.28 | 44.07 | 18.60 |
| 48–54 | 299 | 229 | 1100 | 2.25 | 391 | 6.43 | 54.17 | 108.35 | 44.30 | 18.51 |
| 56–59 | 299 | 231 | 1100 | 2.25 | 408 | 6.33 | 54.40 | 108.43 | 44.34 | 18.63 |
| 64–66 | 301 | 230 | 1100 | 2.25 | 389 | 6.23 | 53.76 | 107.49 | 43.35 | 18.55 |
| 68–72 | 300 | 229 | 1100 | 2.25 | 375 | 6.14 | 53.71 | 108.15 | 43.81 | 18.53 |
| 72–76 | 300 | 229 | 1100 | 2.25 | 373 | 6.04 | 53.84 | 108.58 | 44.15 | 18.54 |
| 76–80 | 300 | 229 | 1100 | 2.25 | 368 | 5.99 | 53.93 | 108.30 | 44.19 | 18.52 |
| 80–84 | 300 | 229 | 1100 | 2.25 | 362 | 5.90 | 54.06 | 108.34 | 44.23 | 18.50 |
| 90–96 | 300 | 229 | 1092 | 2.26 | 325 | 5.99 | 48.67 | 97.38 | 39.86 | 16.83 |
| 96–102 | 299 | 229 | 1092 | 2.26 | 322 | 5.87 | 48.77 | 97.52 | 40.07 | 16.84 |
| 102–108 | 299 | 229 | 1092 | 2.26 | 314 | 5.80 | 48.84 | 97.24 | 40.16 | 16.84 |
| 111–116 | 300 | 230 | 1092 | 2.26 | 317 | 5.71 | 48.41 | 97.09 | 39.22 | 16.82 |
| 116–120 | 300 | 230 | 1092 | 2.26 | 311 | 5.62 | 48.51 | 97.41 | 39.45 | 16.83 |
| 120–124 | 299 | 230 | 1092 | 2.26 | 302 | 5.54 | 48.88 | 97.53 | 39.90 | 16.84 |
| 124–128 | 299 | 229 | 1092 | 2.26 | 296 | 5.48 | 49.03 | 97.82 | 39.98 | 16.82 |
| 128–132 | 299 | 230 | 1092 | 2.26 | 294 | 5.41 | 48.74 | 97.43 | 39.88 | 16.82 |
| 135–138 | 300 | 231 | 1317 | 1.88 | 309 | 5.40 | 48.67 | 97.02 | 39.19 | 16.66 |
| 138–144 | 300 | 229 | 1317 | 1.88 | 294 | 5.35 | 48.85 | 97.71 | 39.77 | 16.67 |
| 144–150 | 299 | 229 | 1317 | 1.88 | 286 | 5.24 | 49.03 | 97.63 | 40.10 | 16.68 |
| 150–156 | 300 | 229 | 1317 | 1.88 | 282 | 5.16 | 48.94 | 96.97 | 40.03 | 16.68 |
| 156–162 | 300 | 229 | 1317 | 1.88 | 277 | 5.13 | 48.73 | 96.70 | 39.69 | 16.68 |
| 162–169 | 300 | 230 | 1317 | 1.88 | 274 | 5.03 | 48.62 | 97.32 | 39.66 | 16.66 |

*The butene-2 feed contained about 6.7 mole % butene-1 and 3.4 mole % n-butane

TABLE IX

| Time hrs | Reactor Press psig | Reactor Temp °F. | Vol of Soln ml | Rh Conc g/L | Ald Rh,hr g/g/hr | B/L | Feed Rate, SCFH CO | H2 | N2 | BU-2* |
|---|---|---|---|---|---|---|---|---|---|---|
| 4–9 | 299 | 230 | 1256 | 1.97 | 523 | 6.97 | 53.98 | 108.05 | 43.93 | 18.64 |
| 9–13 | 299 | 231 | 1256 | 1.97 | 514 | 6.66 | 54.20 | 108.11 | 44.00 | 18.60 |
| 13–17 | 299 | 230 | 1256 | 1.97 | 500 | 6.58 | 54.01 | 107.57 | 43.71 | 18.55 |
| 17–21 | 299 | 230 | 1256 | 1.97 | 488 | 6.58 | 53.74 | 107.27 | 43.50 | 18.54 |
| 21–24 | 299 | 230 | 1256 | 1.97 | 480 | 6.42 | 53.78 | 107.78 | 43.59 | 18.54 |
| 27–30 | 300 | 230 | 1256 | 1.97 | 465 | 6.23 | 53.82 | 108.08 | 43.65 | 18.54 |
| 34–36 | 300 | 230 | 1256 | 1.97 | 453 | 6.03 | 53.91 | 108.00 | 43.68 | 18.53 |
| 40–43 | 300 | 231 | 1131 | 1.89 | 405 | 5.74 | 53.79 | 108.02 | 43.69 | 18.53 |
| 50–54 | 301 | 231 | 1131 | 2.19 | 421 | 5.67 | 53.95 | 108.58 | 43.94 | 18.54 |
| 54–58 | 301 | 230 | 1131 | 2.19 | 404 | 5.59 | 53.88 | 108.32 | 43.90 | 18.54 |
| 58–63 | 301 | 230 | 1131 | 2.19 | 395 | 5.47 | 53.83 | 107.06 | 43.77 | 18.55 |
| 72–77 | 299 | 231 | 1037 | 2.38 | 351 | 5.01 | 54.11 | 108.64 | 44.43 | 18.61 |
| 77–82 | 299 | 230 | 1037 | 2.38 | 342 | 4.91 | 54.35 | 108.99 | 44.73 | 18.63 |
| 82–87 | 300 | 230 | 1037 | 2.38 | 330 | 4.77 | 54.16 | 107.61 | 44.14 | 18.62 |

TABLE IX-continued

| Time hrs | Reactor Press psig | Reactor Temp °F. | Vol of Soln ml | Rh Conc g/L | Ald Rh,hr g/g/hr | B/L | Feed Rate, SCFH CO | H2 | N2 | BU-2* |
|---|---|---|---|---|---|---|---|---|---|---|
| 87–92 | 300 | 230 | 1037 | 2.38 | 316 | 4.62 | 53.86 | 107.78 | 43.76 | 18.59 |

*The butene-2 feed contained about 6.4 mole % butene-1 and 3.5 mole % n-butane

TABLE X

| Time hrs | Reactor Press psig | Reactor Temp °F. | Vol of Soln ml | Rh Conc g/L | Ald Rh,hr g/g/hr | B/L | Feed Rate, SCFH CO | H2 | N2 | BU-2* |
|---|---|---|---|---|---|---|---|---|---|---|
| 27–33 | 301 | 229 | 997 | 2.48 | 102 | 5.45 | 44.92 | 90.01 | 33.93 | 18.09 |
| 33–39 | 301 | 229 | 997 | 2.48 | 102 | 5.44 | 45.18 | 90.40 | 34.20 | 18.10 |
| 39–45 | 300 | 229 | 997 | 2.48 | 101 | 5.42 | 45.22 | 90.45 | 34.36 | 18.11 |
| 45–51 | 301 | 230 | 997 | 2.48 | 102 | 5.43 | 45.13 | 89.83 | 34.18 | 18.11 |
| 56–62 | 299 | 229 | 958 | 2.58 | 102 | 5.22 | 34.18 | 101.22 | 34.11 | 18.10 |
| 64–70 | 299 | 229 | 958 | 2.58 | 98 | 5.09 | 34.13 | 101.09 | 34.03 | 18.11 |
| 70–75 | 299 | 230 | 958 | 2.58 | 96 | 5.00 | 33.89 | 100.71 | 33.74 | 18.08 |
| 80–85 | 301 | 248 | 989 | 2.50 | 121 | 5.41 | 44.94 | 89.97 | 33.84 | 18.08 |
| 85–90 | 301 | 248 | 989 | 2.50 | 115 | 5.29 | 45.01 | 90.12 | 33.90 | 18.07 |
| 90–95 | 301 | 248 | 989 | 2.50 | 110 | 5.16 | 45.32 | 90.32 | 34.00 | 18.08 |
| 95–100 | 301 | 248 | 989 | 2.50 | 108 | 5.07 | 45.08 | 89.87 | 33.70 | 18.06 |
| 106–110 | 200 | 230 | 926 | 2.67 | 38 | 3.80 | 31.43 | 62.93 | 23.88 | 12.67 |
| 110–114 | 201 | 230 | 926 | 2.67 | 38 | 3.79 | 31.48 | 63.00 | 23.89 | 12.68 |
| 114–119 | 201 | 230 | 926 | 2.67 | 37 | 3.78 | 31.47 | 62.95 | 23.86 | 12.67 |
| 122–127 | 300 | 231 | 934 | 2.65 | 66 | 4.15 | 44.97 | 89.90 | 33.93 | 17.87 |
| 127–132 | 300 | 230 | 934 | 2.65 | 65 | 4.06 | 45.16 | 90.34 | 34.13 | 17.87 |
| 132–137 | 301 | 230 | 934 | 2.65 | 64 | 4.05 | 45.32 | 90.60 | 34.28 | 17.89 |

*The butene-2 feed contained about 2.9 mole % butene-1 and 3.8 mole % n-butane

The embodiments of the invention in which an exclusive claim or privilege is claimed are:

1. A continuous process for selectively producing 2-methylbutanal by selectively hydroformylating butene-2 which process comprises contacting, on a continuous process basis, in a hydroformylation zone:

(a) said butene-2;
   (b) with carbon monoxide and hydrogen in the mole ratio of hydrogen to carbon monoxide within the range of 1/1 to 10/1;
   (c) in the presence of an halogen-free rhodium complex catalyst of the empirical formula:

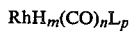
   $$RhH_m(CO)_nL_p \qquad I$$

wherein "Rh" is rhodium, "H" is hydrogen, "CO" carbon monoxide and "L" is a triorganophosphine ligand, and wherein m is 1 or 3, n is from 1 to 3, and p is 1 or 2, the sum of m, n and p being from 4 to 6 said triorganophosphine ligand being selected from the group consisting of trialkylphosphines, tricycloalkylphosphines, wherein each of the three alkyl, including cycloalkyl, groups are alike or different, and each contains from 3 to 10 carbon atoms and wherein said triorganophosphine ligand has a cone angle within the range of 159 to 171 degrees and wherein the frequency of the $A_1$ carbonyl mode of the nickel tricarbonyl complex of the ligand, $Ni(CO)_3L$, in dichloromethane is within the range of 2056.1 to 2061.1 $cm^{-1}$;
   (d) wherein the triorganophosphorus ligand is not in substantial excess such that there is not any substantial amount of free triorganophosphorus ligand;
   (e) at a pressure within the range of about 6 to 30 atmospheres absolute;
   (f) at a temperature within the range of about 80° C. to 150° C.;
   (g) so as to produce hydroformylation products of said butene-2 wherein the mole ratio of 2-methylbutanal to other oxygenated products is at least 4/1; and continuously recovering from said hydroformylation zone said hydroformylation products having a said mole ratio of 2-methylbutanal to other oxygenated products of at least 4/1.

2. The process of claim 1 wherein each of the alkyl, including cycloalkyl, groups of the triorganophosphine ligand are alike.

3. The process of claim 1 wherein the temperature is within the range of about 105° C. to 130° C., wherein the said mole ratio of hydrogen to carbon monoxide is within the range of about 1.5/1 to 3/1, and wherein the pressure is within the range of about 15 to 25 atmospheres absolute.

4. The process of claim 2 wherein the temperature is within the range of about 105° to 130°, wherein the said mole ratio of hydrogen to carbon monoxide is within the range of about 1.5/1 to 3/1, and wherein the pressure is within the range of about 15 to 25 atmospheres absolute.

5. The process of claim 4 wherein said triorganophosphine ligand is tricyclohexylphosphine.

6. The process of claim 4 wherein said triorganophosphine ligand is tri-sec-butylphosphine.

7. The process of claim 4 wherein said triorganophosphine ligand is tri-isopropylphosphine.

8. The process of claim 1 wherein said catalyst has been prepared from a precursor consisting of a rhodium complex with acetylacetonate ligand.

9. The process of claim 3 wherein said catalyst has been prepared from a precursor consisting of a rhodium complex with acetylacetonate ligand.

10. The process of claim 4 wherein said catalyst has been prepared from a precursor consisting of a rhodium complex with acetylacetonate ligand.

11. The process of claim 5 wherein said catalyst has been prepared from a precursor consisting of a rhodium complex with acetylacetonate ligand.

12. The process of claim 6 wherein said catalyst as been prepared from a precursor consisting of a rhodium complex with acetylacetonate ligand.

13. The process of claim 7 wherein said catalyst has been prepared from a precursor consisting of a rhodium complex with acetylacetonate ligand.

14. The process of claim 4 wherein the butene-2 feed passed to said hydroformylation zone is substantially free of butadiene.

* * * * *